United States Patent [19]

Finnieston

[11] 4,393,866

[45] Jul. 19, 1983

[54] TIBIA BRACE

[76] Inventor: Alan Finnieston, 1901 NW. 17 Ave., Miami, Fla. 33125

[21] Appl. No.: 284,019

[22] Filed: Jul. 16, 1981

[51] Int. Cl.³ .............................................. A61F 5/04
[52] U.S. Cl. ................................................ 128/87 R
[58] Field of Search ...................... 128/87 R, 83, 83.5, 128/84 R, 85, 89 R, 90, 91, 80 R, 80 G, 80 F

[56] References Cited

U.S. PATENT DOCUMENTS

| 3,955,565 | 5/1976 | Johnson, Jr. | 128/89 R |
| 4,057,056 | 11/1977 | Payton | 128/89 R |
| 4,320,748 | 3/1982 | Racette et al. | 128/80 F |

Primary Examiner—John D. Yasko
Attorney, Agent, or Firm—Larson and Taylor

[57] ABSTRACT

A tibia brace to be secured about the leg of a wearer and including a posterior segment and an anterior segment sized for intermating nested relation of the anterior segment with respect to the posterior segment for clam shell type interengagement of the segments about the leg of a wearer to lend support to it and wherein a plurality of straps may be provided to maintain the two in relation with one another about the leg of a wearer and wherein a vertically adjustable member is provided to orient and to locate the brace with respect to the wearer's leg.

7 Claims, 4 Drawing Figures

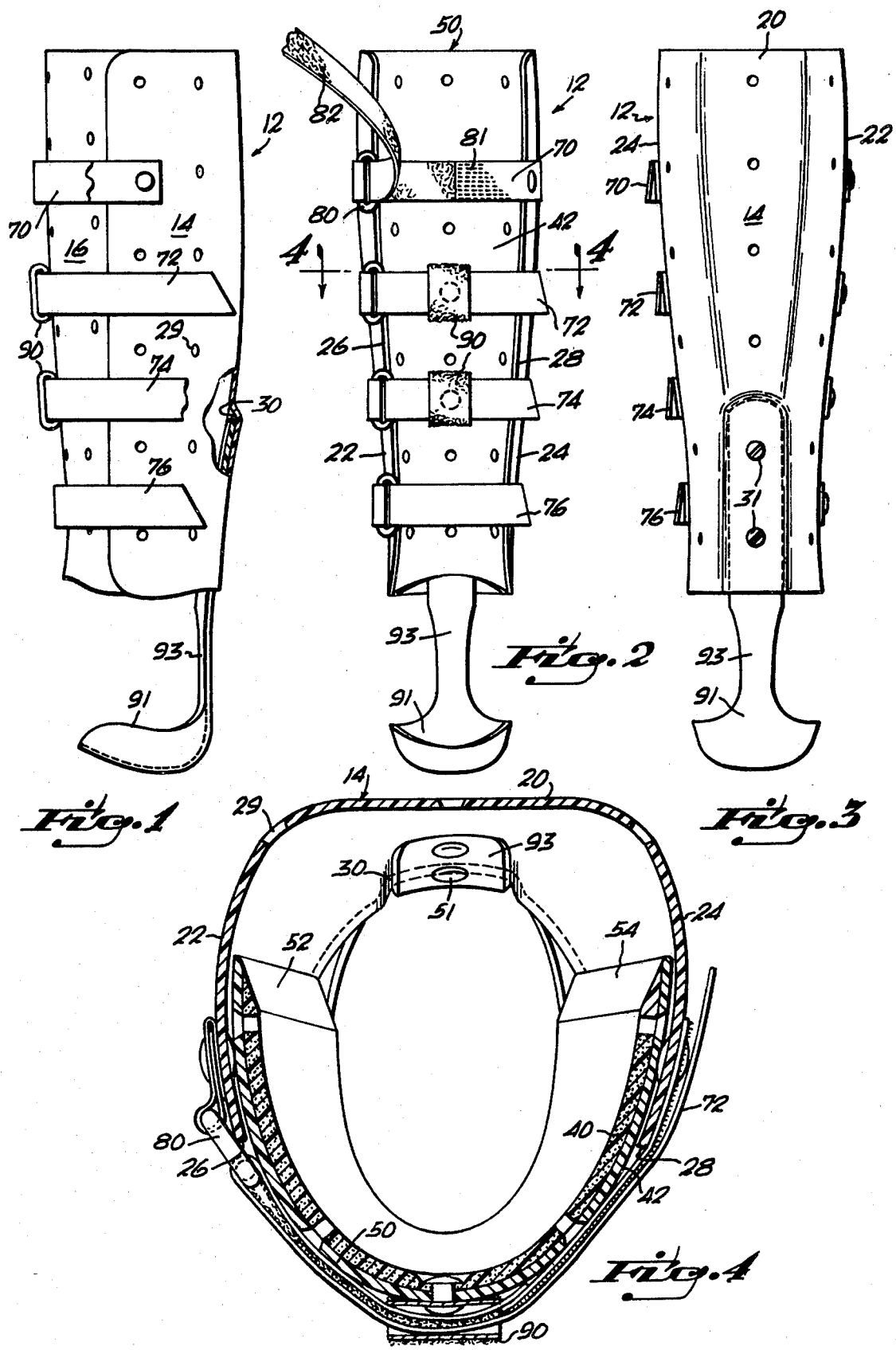

TIBIA BRACE

FIELD OF THE INVENTION

This invention relates to a tibia brace.

BACKGROUND OF THE INVENTION

In the past there have been numerous types of devices which have been utilized for a person having an injured or broken leg such as the well-known plaster cast. This invention is of a tibia brace which is adapted to be secured about the leg of a wearer and wherein a first and a second or rather, a posterior and an anterior segment are provided for clamping or clam shell type interengagement with one another about the leg of the wearer to apply pressure to the flesh so as to support the tibia. The device includes an adjustment means to adjust the amount of pressure which is applied by the two segments when in nested relation with one another and about the leg of a wearer and preferably includes an adjustment means for adjusting the height of the device and maintaining and orienting it in a proper relationship which may be in the form of a heel cup which receives the heel of a wearer.

OBJECTS OF THE INVENTION

It is a general object of this invention to provide a tibia brace comprising a posterior segment and an anterior segment which intermate with one another and which are maintained in position by keeper means which may be in the form of a strap, preferably of Velcro, secured to the posterior segment and wherein means to locate the brace vertically on the leg of a wearer and circumferentially orient it so as to provide support to the user.

It is another object of this invention to provide a tibia brace of the type set forth wherein the base of the U-shaped posterior segment is provided with a flat surface to apply pressure to the flesh in the posterior side of the leg of a wearer to exert a stabilizing support to a tibia about which the brace is secured.

It is another object of this invention to provide a brace of the type described wherein a plurality of perforations are provided in a posterior and anterior segment to accommodate breathing and use of the device.

It is another object of this invention to provide a device of the type described wherein a liner means is provided along the anterior segment to provide a padding along the relatively tender shin bone of a user and preferably wherein there is an adjustment means provided to adjust the force exerted by the segments when in telescoping relation with one another, that is with the anterior brace received within the posterior brace and in tight clamping relation about the leg of a wearer.

In accordance with these and other objects which will become apparent hereinafter, the instant invention will now be described with reference to the accompanying drawings in which:

DESCRIPTION OF THE DRAWINGS

FIG. 1 is a side elevation view which is partly broken away and illustrating the tibia fracture brace;

FIG. 2 is a front elevation view of the tibia fracture brace;

FIG. 3 is a rear elevation view of the tibia fracture brace;

FIG. 4 is a view in cross section taken on the plane indicated by the line 4—4 of the tibia fracture brace.

DESCRIPTION OF THE PREFERRED EMBODIMENT

Referring to the drawings wherein like reference characters designate like or corresponding parts throughout the several views and referring particularly to the tibia brace generally designated by the numeral 12. It is composed of a posterior segment 14 and an anterior segment 16 which are intermated into clam shell relation, so that one is slidable with respect to the other, i.e., expandable in a horizontal direction, generally as seen in FIG. 4 to accommodate larger and smaller girths of legs so that one size generally, fits all.

Generally speaking, the posterior segment is generally U-shaped in cross section, see FIG. 4, and of a length of about between 10 inches and 14 inches. The base 20 of the U-shaped portion is generally flat and the side walls 22 and 24 are curved smoothly and fairly to spaced terminal ends as at 26 and 28 which are spaced from one another. The material is of plastic within the rigid range and is in a flexible relatively thin construction so that the mouth between the terminal ends 26 and 28 can be flexed or expanded by hinged movement of the side walls relative to the base. This segment 14 is perforated as indicated by the holes of which 29 is representative, and which are arranged in a pattern throughout the posterior segment.

The mating anterior segment is generally designated by the numeral 16; and it is seen that it is generally U-shaped but is somewhat rounded or curved so that as seen in cross section it might be considered to be generally C-shaped. It has an outside surface and an inside surface. The inside surface is lined with foam material as is generally designated by the numeral 40. As best seen in FIGS. 1-3, the upper edge is somewhat larger that is at the top edge 50 than the lower or bottom end so that the brace is somewhat tapered to conform to the leg of a wearer. This segment is also of rigid plastic material in a flexible construction. The exterior surface designated by the numeral 42 defines a relatively thin plastic skin which is sturdy. Preferably the liner is of foam material and beveled as at 52 and 54.

In use, the anterior segment fits over the long bone of the leg of a wearer while the base of the posterior section overlays the flesh along the rear of a wearer's leg. As seen in FIGS. 1 through 3, keeper means are provided which may be of a plurality of straps such as 70, 72, 74 and 76. One end of each of the straps is adapted to be received in a buckle, such as 80, fixed along and adjacent one of the mouth edges. The other end of these straps are secured to the opposite edge 28 by suitable means such as that shown and preferably these straps are of Velcro, each with a portion adjacent one end which comprises J hooks and another portion which comprises loops to intermate with the J hooks providing an adjustable strap, as indicated by the numerals 81 and 82.

In any event, once arranged about the leg of a wearer, the straps are tightened. Preferably, the anterior segment includes a plurality of loops, such as that designated by the numeral 90, which serve to maintain the posterior segment and anterior segment in generally mating relation, resisting relative vertical displacement of the two segments when in position on the leg of a wearer. The two segments are of substantially the same length. Thus, there is provided a fastener means or keeper means to maintain the two pieces together in clamped relation about the leg of a wearer.

To maintain the proper height of the device, a heel cup generally designated by the numeral 91 is provided and extending upwardly from it there is provided a stem 93 which is secured to the base of the posterior section as by a recessed rivet 51. In a preferred embodiment the base of the U is provided with a recessed zone as at 30 so that the interior is smooth. It is secured by screws such as 31 and a height adjustment means may be provided by providing slots within the stem, not shown, or any other suitable means.

While this invention has been shown and described in what is considered to be a practical and preferred embodiment, it is recognized that departures may be made within the spirit and scope of this invention which is, therefore, not to be limited except as set forth in the claims which follow within the doctrine of equivalence.

What is claimed is:

1. A tibia brace to nest about and to be secured about a wearer's leg, said brace having anterior and posterior segments, extending from a point below the knee of the wearer to a point above the ankle of the wearer, said posterior segment with an interior and an exterior main surface, said interior surface being adapted to confront the posterior surface of the leg of the wearer, said posterior segment being of relatively thin rigid plastic material and said segment having an upper end and a lower end zone, said upper end and said lower end zone being spaced from one another a predetermined distance of between about 10 inches to 14 inches, said posterior segment being generally U-shaped as seen in cross section defining a base and a pair of spaced side walls extending in generally curved relation from the base, the upper end being greater in size than the lower end zone sizing the posterior segment for mating along the leg of a wearer, each side wall having a terminal end edge spaced from one another and defining a mouth of predetermined normal unflexed dimension and yieldable to expansion or contraction to manipulate the mouth;

said anterior segment having an inside surface and an outside surface with an upper end and a lower end and being generally C-shaped as seen in cross section, said upper end and said lower end being spaced from one another a companionate distance to mate with the distance between the upper end and lower end zone of the posterior segment in clamping relation along the anterior part of the leg of a wearer;

keeper means to stabilize the segments in mating relation with one another with a portion of the anterior segment within the mouth defined by the posterior segment and in nesting relation about and along the length of the leg of a wearer to provide support around the entire periphery of the leg without gaps in the engagement of the leg and interior surfaces of the posterior and anterior segments; and means to locate and orient the brace vertically and circumferentially with respect to the leg of a wearer and said means to locate including a portion to receive the heel of the wearer to stabilize the location of the brace, said last named means being secured to the posterior segment and said heel receiving portion extending forwardly from a point spaced vertically below the lower ends of said posterior and anterior segments and lying substantially between a downward extension of the vertical surfaces of said segments, whereby the knee and ankle joints of the wearer are unrestrained by said tibia brace and said means to locate and orient the brace supports the brace in proper vertical position on the leg of the wearer.

2. The device as set forth in claim 1 wherein the base of said posterior segment is flat.

3. The device as set forth in claim 1 and claim 2 wherein said posterior segment is provided with a pattern of spaced holes therethrough.

4. The device as set forth in claim 1 wherein the base of said posterior segment at said lower end zone is provided with a recess in the interior surface and said means to locate the brace comprises a stem sized to nest within said recess and means to secure said stem to said base within said recess.

5. The device as set forth in claim 1 wherein said anterior segment is provided with a liner means overlaying said interior surface and a plurality of holes are provided through said anterior segment in spaced relation from one another.

6. The device as set forth in claim 1 wherein said keeper means comprises a plurality of straps, each strap having a first end and a second end and means to secure the first end of each strap to the posterior segment along one of the terminal ends and buckle means along the other of said side walls adjacent said mouth for hooked-up relation of said loops about said anterior segment for snugly nesting said anterior segment into conforming relation about the leg of a wearer and in mating engagement with the posterior segment.

7. The device as set forth in claim 1 and claim 6 wherein a loop is provided along said anterior segment in spaced relation to receive each of said straps.

* * * * *

UNITED STATES PATENT AND TRADEMARK OFFICE
CERTIFICATE OF CORRECTION

PATENT NO. : 4,393,866
DATED : July 19, 1983
INVENTOR(S) : Alan Finnieston et al.

It is certified that error appears in the above-identified patent and that said Letters Patent is hereby corrected as shown below:

On the title page, item [76] should read

-- [76] Inventors: Alan Finnieston, 1901 NW. 17 Ave., Miami, Fla. 33125 and
Joseph B. Zagorski, 440 Castania Coral Gables, Fla. 33134 --.

Signed and Sealed this

Twenty-second Day of November 1983

[SEAL]

Attest:

GERALD J. MOSSINGHOFF

Attesting Officer

Commissioner of Patents and Trademarks